United States Patent [19]

Handa et al.

[11] 4,301,803

[45] Nov. 24, 1981

[54] BALLOON CATHETER

[75] Inventors: Hajime Handa; Yasuhiro Yonekawa; Sen Yamagata; Waro Taki, all of Kyoto; Yoshito Ikada; Hiroo Iwata, both of Uji, all of Japan

[73] Assignee: Kuraray Co., Ltd., Kurashiki, Japan

[21] Appl. No.: 80,037

[22] Filed: Sep. 28, 1979

[30] Foreign Application Priority Data

Oct. 6, 1978 [JP] Japan ............... 53-123914
Mar. 19, 1979 [JP] Japan ............... 54-32645

[51] Int. Cl.$^3$ .......................... A61M 25/00
[52] U.S. Cl. ............................... 128/349 B
[58] Field of Search ........... 128/344, 349 B, 349 BV, 128/656, 657

[56] References Cited

U.S. PATENT DOCUMENTS 3,985,601 10/1976 Panagrossi ............ 128/349 B
4,029,104 6/1977 Kevber ................ 128/656
4,188,954 2/1980 Patel et al. .......... 128/349 B
4,210,478 7/1980 Shoney ............... 128/349 B

OTHER PUBLICATIONS

Advances in Cerebral Angiography-Djindjian Ed. Salamon pp. 192-197, 1975.

Primary Examiner—Hiram Bernstein
Attorney, Agent, or Firm—Oblon, Fisher, Spivak, McClelland & Maier

[57] ABSTRACT

Disclosed is a balloon catheter including a catheter and a balloon bonded to the catheter through an adhesive in which the outer surface of the balloon is contiguous to the outer surface of the catheter through a smooth surface. In this balloon catheter, the balloon is tightly fixed to the catheter and there is no risk of separation of the balloon. Further, since the balloon catheter has a smooth surface in the connecting portion, insertion of the balloon catheter into a blood vessel and withdrawal of the balloon catheter from the blood vessel can be performed very easily and smoothly. Accordingly, this balloon catheter can be used very advantageously for the angiography.

7 Claims, 3 Drawing Figures

BALLOON CATHETER

BACKGROUND OF THE INVENTION

1. Field of the Invention

The present invention relates to a balloon catheter. More particularly, the invention relates to a balloon catheter for use in the angiography.

2. Description of the Prior Art

The main object of the angiography in which a contrast medium is injected in a blood vessel and the flow of the injected contrast medium is observed according to the roentgenography is to diagnose not only expansion of the morbid state in the blood vessel per se but also expansion of the morbid state to various organs and surrounding textures by a compressed vessel image and an infiltrated vessel image. Improvements have been perpetually made on this angiography. Among these improvements, development of the Seldinger method is important and significant. More specifically, before development of this method, insertion of catheters into blood vessels had been performed by surgical operations, but following the Seldinger method development, the selective angiography has made a rapid progress because insertion of catheters into blood vessels can be performed percutaneously with ease (without surgical operations) when this method is adopted.

Recently, there has been adopted and practised the selective angiography in which the top end of a catheter inserted in the main artery or main vein is introduced even into a primary or secondary branch of the main artery or main vein and the objective blood vessel is selectively visualized. According to this method, overlap visualization of the objective blood vessel with other blood vessles can be prevented, and the roentgengraphy can be performed with an improved visualizing capacity because dilution of the contrast medium in the blood vessel is prevented. Accordingly, the diagnosis precision is remarkably improved as compared with the conventional method in which a catheter is inserted in the main artery or main vein. As a procedure for practising this selective angiography, there has ordinarily been adopted a method in which a top of the catheter is first bent and then the catheter is inserted into the objective blood vessel while turning, advancing and retreating the catheter under X-ray fluoroscopy.

Indeed, the diagnosis precision is increased in this selective angiography as compared with the conventional angiographical methods. However, even according to this selective angiography, it is impossible to visualize minute blood vessels or insert a catheter beyond crooked and indented blood vessels if conventional catheters are employed. For example, it is impossible to guide a catheter to the intracranial artery. It is considered that this will be possible if a balloon catheter having a fine diameter is employed. There has been the balloon catheters in which a catheter and a balloon are fixed together by a silk yarn or rubber yarn [see, for example, Neuroradiology, 9, 145–156 (1975)], and these conventional catheters involve a risk of separation of the balloon from the catheter when the balloon is inflated in the blood vessel. Moreover, a stepwise change of the thickness of the balloon is caused in an attachment portion where the balloon is attached to the catheter and the resulting step portion hinders insertion or withdrawal of the balloon catheter and there is a risk that the blood vessel will be damaged by this step portion. Furthermore, the catheter of the balloon catheter to be used for the above purpose should have such an appropriate flexibility as will facilitate insertion of the catheter into the blood vessel and movement of the catheter in the blood vessel.

SUMMARY OF THE INVENTION

It is therefore a primary object of the present invention to provide a balloon catheter which can be very easily inserted into the blood vessel and withdrawn therefrom very easily without fear of separation of the balloon.

Another object of the present invention is to provide a balloon catheter which enables a super-selective angiography, when inserted into the blood vessel.

In accordance with the present invention, these objects can be attained by a balloon catheter including a catheter and a balloon fixed to the catheter through an adhesive in which the outer surface of the balloon is contiguous to the outer surface of the catheter through a smooth surface.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts through the several views and wherein.

DETAILED DESCRIPTION OF THE PREFERRED EMBODIMENTS

The balloon catheter of the present invention will now be described in detail by reference to embodiments illustrated in the accompanying drawings.

Figure 1:
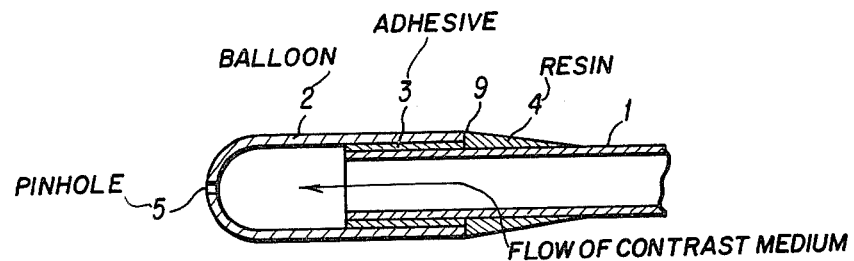
FIG. 1 is a view showing the longitudinal section of the top end portion in one embodiment of the balloon catheter of the present invention.

Referring to FIG. 1, the balloon catheter of the present invention includes a tubular catheter 1 and an inflatable balloon 2 which is mounted on one end of the catheter 1 so that a fluid is introduced into the balloon 2 from the catheter 1. The other end of the catheter 1 is extended along a predetermined length (the length is appropriately selected according to the intended use) (not shown). Ordinarily, an injection needle is inserted into the other end of the catheter so that a fluid is introduced into the catheter by a syringe.

In the balloon catheter of the present invention, in order to fix the balloon tightly to the catheter, the balloon 2 is attached to the catheter 1 so as to cover the outer surface of the end portion of the catheter 1 and is bonded in this state by an adhesive 3. Furthermore, a resin layer 4 is formed and arranged as shown in the drawings, whereby a step 9 formed by the thickness of the balloon 2 in the balloon attachment portion is eliminated and the outer surface of the balloon 2 is made contiguous to the outer surface of the catheter 1 through a smooth surface in the attachment portion and the periphery thereof. It is preferred that the resin layer be formed so that the outer diameter of the balloon attachment portion is gradually decreased to the outer diameter of the catheter. Furthermore, a pinhole 5 is formed on the top end of the balloon for injection of a contrast medium into the blood vessel. In some uses, however, this pinhole need not be formed.

Figure 2:
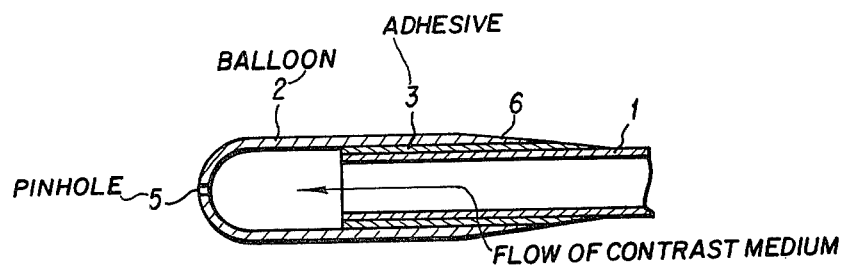
FIG. 2 is a view showing the longitudinal section of the top end portion in another embodiment of the balloon catheter of the present invention.

In an embodiment shown in FIG. 2, the end portion 6 of the balloon 2 is cut to form a smooth inclined surface, and the inner surface of this end portion 6 is fixed to the outer surface of the top end of the catheter 1 by an adhesive 3. When this arrangement is adopted, even if a resin layer 4 as shown in FIG. 1 is not formed, the outer surface of the balloon can be made contiguous to the outer surface of the catheter through a smooth inclined surface.

Figure 3:
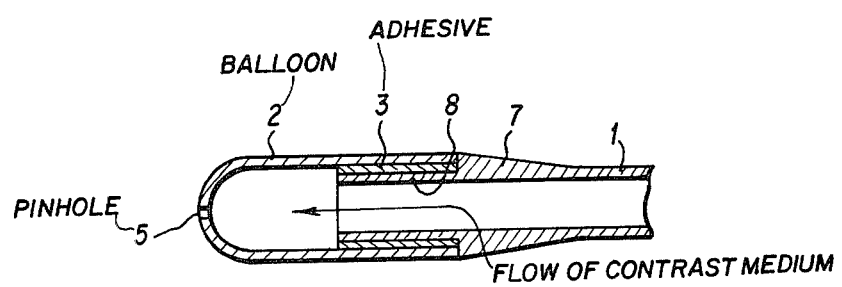
FIG. 3 is a view showing the longitudinal section of the top end portion in still another embodiment of the balloon catheter of the present invention.

In an embodiment shown in FIG. 3, a projection 7 having a smooth inclined surface is formed on the outer surface of the top end of the catheter 1, and the inner surface of the balloon 2 is fixed to the outer surface of the topmost end 8 of the catheter 1 by an adhesive 3. When this arrangement is adopted, even if a resin layer 4 as shown in FIG. 1 is not formed, the outer surface of the balloon can be made contiguous to the outer surface of the catheter through a smooth inclined surface as in the embodiment shown in FIG. 2.

Each of the foregoing three embodiments is a preferred embodiment of the balloon catheter of the present invention. Among these embodiments, the embodiment shown in FIG. 1 is most preferred because the balloon catheter can be manufactured most simply.

In the present invention, the material of the balloon is not particularly critical. Any of the materials having an appropriate elasticity, being inflatable in the blood vessel by a fluid fed through the catheter and being capable of standing disinfection process can be used. Natural rubbers, synthetic rubbers silicone rubbers and other elastomers which have heretofore been used as balloon materials are preferably employed in the present invention. The shape and size of the balloon are determined according to the kind of the objective vessel. Ordinarily, a balloon having a cylindrical cap-like shape as shown in the drawings is employed. In order to enable the balloon to be inserted even into crooked and indented minute blood vessels, it is preferred that the thickness of the balloon in the non-inflated state be as small as possible, for example, less than $500\mu$, particularly less than $200\mu$. However, in order for the balloon to exert its function sufficiently without breakage, it is necessary that the thickness be more than $20\mu$, preferably more than $50\mu$. Because of this thickness, a step is formed when the balloon is attached to the catheter. Such balloon is ordinarily prepared by applying a conventional rubber latex to a mold by a dipping method or electrodeposition method and vulcanizing the rubber latex. A pinhole 5 as shown in the drawings may be formed at an appropriate position (for example, the top end) of the balloon, whereby injection of a contrast medium into the intended vessel branch or local administration of a chemical such as a carcinostatic agent to a focus can be performed. The balloon is sufficiently inflated by a fluid injected through a syringe and is allowed to float and move in the stream of the blood, unless the diameter of this pinhole 5 is excessively increased. When the balloon catheter is used to clog a certain blood vessel branch for shutting flow of the blood into this branch or to clog a morbid portion such as an aneurysm, this pinhole 5 is not formed on the balloon, and the balloon is inflated to an appropriate size and is caused to float and move in the blood vessel to the intended position.

Any type of catheter can be used in the present invention, so far as it can be inserted in the blood vessel. Ordinarily, a fine tube (for example, a hollow fiber) having an outer diameter of 100 to $1000\mu$, preferably 200 to $700\mu$ and a wall thickness of 10 to $400\mu$, preferably 10 to $200\mu$ is used. The material of the catheter is not particularly critical. For example, there can be used polyethylene, polyamides, polyvinyl chloride, polyvinyl alcohol, acetalized polyvinyl alcohol having a degree of acetalization of 10 to 50 mol % and ethylene-vinyl alcohol copolymer having an ethylene content of 10 to 60 mol %. Fine tubes as catheters can easily be prepared from these polymeric materials according to known polymer molding techniques. In order to form a fine tube that can easily be inserted even into crooked and indented fine blood vessels, it is preferred to use a material having a Young's modulus of 1 to 100 Kg, particularly 2 to 20 Kg, in the wet state as the fine tube. In the instant specification, the Young's modulus is a value as measured in water at 25° C. at a pulling speed of 10 cm/min end a sample length of 5 cm by using an ordinary tensile tester. If the Young's modulus is lower than 1 Kg, the fine tube is too flexible and it is very difficult to move the fine tube in an introducing catheter. If the Young's modulus exceeds 100 Kg, the fine tube becomes too hard and it is very difficult to move the fine tube in crooked and indented fine blood vessels. Any of materials having a Young's modulus within the above-mentioned range can be used for the production of a fine tube as the catheter. Among these materials, acetalized polyvinyl alcohol (polyvinyl alcohol will be abbreviated to "PVA" hereinafter) is most preferred as the material of the fine tube.

Such acetalized PVA catheter can be prepared by forming a hollow fiber or tube having desired inner and outer diameters from PVA having a degree of polymerization of from 1000 to 3000 by a wet or dry method and acetalizing the hollow fiber or tube.

An acetalization method customarily adopted in the manufacture of PVA type synthetic fibers can be applied to the above-mentioned acetalization. As the aldehydes that are used for the acetalization, there can be mentioned, for example, monoaldehydes such as formaldehyde, acetaldehyde, propionaldehyde and benzylaldehyde and dialdehydes such as glyoxal, glutaraldehyde and terephthalaldehyde. Among them, formaldehyde and glutaraldehyde are preferred. The degree of acetalization is ordinarily in the range of from 10 to 50 mol %, though the preferred degree of acetalization differs to some extent depending on the kind of the aldehyde used.

The formalization process will now be described as one instance of the process for the preparation of acetalized PVA catheters.

A PVA hollow fiber or tube is prepared from an aqueous solution of PVA having a concentration of about 15% according to the wet method using an aqueous solution of sodium sulfate as a coagulating bath while drafting the extrudate. The PVA hollow fiber or tube is subjected to the dry heat treatment at 200° to 240° C. for several minutes and formalized for 40 to 60 minutes at 50° to 70° C. in a formalizing bath containing 150 to 250 g/l of sodium sulfate, 150 to 250 g/l of sulfuric acid and 40 to 60 g/l of formaldehyde. The degree of formalization is in the range of 30 to 40 mol % in the so obtained PVA hollow fiber or tube.

The so obtained acetalized PVA catheter has a Young's modulus included in the above-mentioned range and is excellent in both the dry tensile strength and the wet tensile strength. Accordingly, the thickness can be decreased though the diameter is very small and the catheter has such an appropriate flexibility that it is not readily bent in water. Therefore, this catheter is preferably used in the present invention. Moreover, this acetalized PVA catheter has an advantage that it can sufficiently resist the boiling water treatment for disinfection. When the catheter is subjected to steam sterilization, an acetalized PVA having a high heat resistance, which has been crosslinked with a dialdehyde, is preferably employed.

The kind of the adhesive (3 in FIG. 1) used for fixing the balloon to the catheter is not particularly critical, so far as it can fix and bond the balloon to the catheter so tightly that the balloon is not separated from the catheter, and an appropriate adhesive is selected from commercially available adhesives, particularly commercially available medicinal adhesives such as cyano acrylate type adhesives. In order to attain high adhesion, it is preferred to adopt a method in which the surface of the catheter is preliminarily treated with a chromic acid or plasma jet and the balloon is bonded to the catheter by an adhesive.

The resin layer (4 in FIG. 1) for formation of a smooth surface in the connecting portion between the outer surface of the balloon and the outer surface of the catheter, which is illustrated in FIG. 1, may be formed by using an adhesive or sealant capable of bonding the balloon tightly to the catheter. As such adhesive or sealant, there can be mentioned, for example, an epoxy resin, a urethane resin and a silicone rubber. The same adhesive may be used for the adhesive layer 3 and the resin layer 4. The resin layer can be formed by manually applying the resin to the periphery of the balloon attachment portion so that the outer surface of the balloon is made contiguous to the outer surface of the catheter through a smooth surface, that is, no step is formed in the balloon attachment portion and the balloon attachment portion is smoothly expanded while drawing a gradual curve or line.

The balloon catheter of the present invention is subjected to disinfection according to customary procedures and is then used. When the balloon catheter is kept inserted in the blood vessel for a long period of time and there is a risk of formation of thrombi on the surface of the balloon catheter, it is preferred to apply an anticoagulant such as heparin or a fibrinolytic enzyme such as urokinase to the surface in advance.

As the method for inserting this balloon catheter into the blood vessel, there can be mentioned a method in which a catheter having an inner needle or a hollow needle (about 1 to 2 mm in outer diameter) (such as an intravenous catheter or Seldinger needle) is inserted into the blood vessel, a guide wire is passed through the hollow needle, the hollow needle is withdrawn, an introducing catheter is inserted by using the guide wire as a support, the guide wire is then withdrawn and the balloon catheter is inserted into the introducing catheter.

The balloon of the balloon catheter inserted into the blood vessel is guided to a desired position by the blood stream. Then, a contrast medium is injected into the balloon and is jetted into the blood vessel from the pinhole. The selective angiography of the blood is accomplished in this state by roentgenography. Furthermore, the balloon catheter is inserted in the blood vessel and guided to a desired position, and while the blood stream is temporarily shut in this blood vessel by inflating the balloon by a physiological saline solution, a contrast medium is injected by using another means (for example, by passing the contrast medium through an introducing catheter) and the selective angiography is accomplished by the roentgenography. These angiographic methods will now be described in detail in Examples 4 to 8 given hereinafter. Moreover, the balloon catheter can be used for local administration of a chemical or medicine.

By virtue of the above-mentioned specific structure, the balloon catheter of the present invention can attain the following prominent effects.

(1) Since the balloon is tightly fixed to the catheter, there is no risk of separation of the balloon.

(2) Since the outer surface of the balloon is contiguous to the outer surface of the catheter through a smooth surface, the balloon catheter is not caught on the top end of an introducing catheter and can be smoothly withdrawn. Furthermore, when the balloon catheter is inserted into the blood vessel, it does not damage the blood vessel or the like. After the angiography or clinical treatment, the balloon is contracted and the balloon is gradually withdrawn. If there is no smooth inclined surface in the boundary between the balloon and the catheter, the balloon is caught on the introducing catheter at this withdrawal operation, and withdrawal of the balloon becomes impossible or the balloon is separated from the catheter and there is a risk that the balloon acts as embolizing means. However, in the balloon catheter of the present invention, such disadvantage is not observed at all.

(3) Furthermore, since the catheter is composed of a fine hollow fiber having a specific Young's modulus and an appropriate flexibility, the selective or superselective angiography of minute blood vessels such as the intracranial artery can be performed effectively by using the balloon catheter of the present invention. Moreover, local injection of a medicine or chemical into a specific desired locus is made possible by the use of the balloon catheter of the present invention. Especially, in the field of the neurosurgery, percutaneous catheterization of the intracranial artery, which is impossible according to the conventional techniques, can be conveniently performed when the balloon catheter of the present invention is used. Accordingly, an epoch-making great progress can be attained in either the diagnosis or the clinical treatment by the use of the balloon catheter of the present invention.

(4) Since the structure of the balloon catheter of the present invention is very simple, it can be manufactured very easily, and the manufacturing cost can be remarkably reduced.

The present invention will now be described in detail by reference to the following examples that by no means limit the scope of the invention.

EXAMPLE 1

A balloon catheter as shown in FIG. 1 was prepared according to the following procedures.

A commercially available curing additive was added to a natural rubber latex, and the resulting composition was thinly applied to a copper mold having an outer diameter of 0.6 mm by the electro-deposition method. The mold was placed in air maintained at 110° C. for 15 minutes to effect curing, whereby a balloon 2 having a thickness of 100μ was prepared. It was dipped in ethanol to remove soluble matters sufficiently. A polyethylene tube having a Young's modulus of 2.4 Kg (as measured at 25° C. in water) and having an outer diameter of 600μ and a thickness of 180μ, the top end portion of which had been subjected to a chromic acid treatment, was used as a catheter 1. As shown in FIG. 1, the balloon 2 was attached to the top end of the tube 1 and was bonded thereto by a cyano acrylate type adhesive 3. An epoxy resin 4 was coated on the outer surface of the catheter in the periphery of the balloon attachment portion to form such a resin layer that the outer surface of the balloon made was smoothly contiguous to the outer surface of the catheter in the balloon attachment portion and the periphery thereof, and the so formed resin layer was solidified. A pinhole 5 is formed on the top end of the balloon of the so obtained balloon catheter. The balloon catheter was disinfected with an alcoholic solution or chlorhexidine alcohol and was used for the clinical treatment. In this balloon catheter, the balloon was sufficiently bonded to the catheter, and a sufficient strength was retained even after the balloon was subjected to inflation and contraction repeatedly.

EXAMPLE 2

A balloon catheter as shown in FIG. 1 was prepared according to the following procedures.

A commercially available curing additive was added to a natural rubber latex, and the viscosity was adjusted. The composition was thinly coated on a stainless steel mold having an outer diameter of 0.4 mm according to the dipping method. The mold was placed in air maintained at 120° C. for 10 minutes to effect curing, whereby a balloon 2 having a thickness of 100μ was formed. The so prepared balloon was bonded by using a cyano acrylate type adhesive 3 to the top end of a PVA hollow fiber 1 having a Young's modulus of 2.5 Kg (as measured in water at 25° C.) and having an outer diameter of 400μ, and a thickness of 100μ, which had been heat-treated at 190° C. for 10 minutes. Then, an epoxy type adhesive 4 was coated to the periphery of the balloon attachment portion to form a smooth surface and then the adhesive 4 was solidified. This Example was different from Example 1 in the point that the top end portion of the hollow fiber 1 as the catheter was not subjected to any pre-treatment. However, very good bonding was attained between the balloon and the catheter.

EXAMPLE 3

A PVA hollow fiber having an outer diameter of 400μ and a thickness of 50μ in the dry state was immersed in a liquid mixture containing 50 g/l of formaldehyde, 150 g/l of sulfuric acid and 150 g/l of sodium sulfate and treated at 60° C. for 1 hours. The hollow fiber was sufficiently washed with water after the treatment to obtain a formalized PVA hollow fiber having a degree of formalization of 25 mol %. The hollow fiber had an outer diameter of 400μ and a thickness of 50μ in the dry state. The Young's modulus of the hollow fiber in the wet state at 25° C. was 3.0 Kg. It was found that the hollow fiber could resist the boiling water treatment for disinfection.

A balloon catheter was prepared in the same manner as described in Example 1 except that the so obtained hollow fiber was used instead of the polyethylene tube used in Example 1. Although the thickness of this formalized PVA hollow fiber was smaller than those of the tube and hollow fiber of Examples 1 and 2, it had an appropriate Young's modulus and the balloon catheter formed by using this hollow fiber had an appropriate flexibility.

EXAMPLE 4

A patient was kept lying on his back on an angiographical bed and the right inguinal region was disinfected. The right femoral artery was punctured by an intravenous teflon sheathed needle of gauge No. 19. An inner needle was withdrawn and an outer needle was inserted into the femoral artery.

Then, a guide wire (Cook TSF 35, 145 cm) was passed through the intravenous catheter and inserted in the formal artery. Then, the outer needle of the intravenous catheter was withdrawn, and a sheath introducer (Cook TSSW 6.3 F6) was inserted by using the guide wire as a support. The inner tube of the sheath and the guide wire were withdrawn while only the outer tube of the sheath was left in the blood vessel.

A catheter (B-D Formocath No. 7650, inner diameter=1.6 mm, outer diameter=2.1 mm) having the top end bent by thermal molding was passed through the sheath and inserted into the femoral artery. Then, a guide wire (TSF 35, 145 cm) was inserted into the catheter and the catheter was guided in the right internal carotid artery by operating the guide wire under X-ray fluoroscopy. This catheter will hereinafter be referred to as "introducing catheter" for convenience.

The balloon catheter prepared in Example 1 was inserted into the introducing catheter, and when the top end of the balloon was introduced into the internal carotid artery, the balloon was inflated by a contrast medium (angiografin) and the balloon was guided into the middle cerebral artery by utilizing the blood stream. Incidentally, a pinhole had been formed on the top end of this balloon. The balloon catheter had been dipped in a physiological saline solution containing 6000 V/3 ml of urokinase for about 1 hour in advance.

While the balloon was inflated by a physiological saline solution to shut temporarily the blood stream in the middle cerebral artery, 8 cc of a contrast medium (angiografin) was injected through the introducing catheter and the roentgenography was continuously conducted. The middle cerebral artery was not visualized but only the anterior cerebral artery was visualized.

After the angiography, the balloon catheter could be withdrawn smoothly without being caught on the top end of the introducing catheter.

EXAMPLE 5

A patient different from the patient treated in Example 4 was treated in the same manner as described in Example 4. The introducing catheter was guided into the right internal carotid artery through the femoral artery. Then, the balloon catheter prepared in Example 1 was inserted, and while the balloon was inflated, the balloon catheter was guided to the middle cerebral artery. The balloon catheter was inflated by a physiological saline solution to shut temporarily the blood stream in the middle cerebral artery. Simultaneously, 8 cc of a contrast medium was injected through the introducing catheter. The selective angiography of the anterior cerebral artery was carried out in this state. Only the anterior cerebral artery was selectively visualized. The balloon catheter could be withdrawn very easily.

EXAMPLE 6

A patient different from the patients treated in Examples 4 and 5 were treated in the same manner as described in Examples 4 and 5. The introducing catheter was inserted through the femoral artery. Under X-ray fluoroscopy, the introducing catheter was guided to the right external carotid artery. The balloon catheter having a pinhole formed on the top end thereof, which had been prepared in Example 1, was inserted and guided into the superficial temporal artery while being inflated. Then, 2 cc of a contrast medium was injected in the balloon catheter and by utilizing the contrast medium jetted from the pinhole, the superficial temporal artery on the side distal from the balloon was subjected to the selective angiography. After the angiography, the balloon catheter could be smoothly withdrawn without separation of the balloon.

EXAMPLE 7

A patient was kept lying on his back on an angiographical bed and the left neck was disinfected. The left carotid artery was punctured by an intravenous teflon sheathed needle of gauge No. 19 having a length of 9 cm and an outer needle of the catheter was advanced to the left internal carotid artery. The balloon catheter prepared in Example 2 was inserted into the internal carotid artery through the intravenous catheter. The balloon catheter was advanced while the balloon was inflated, and simultaneously, the right carotid artery was pressed by the hand to shut the blood stream in the right carotid artery, whereby left-to-right shunt was caused through the anterior communicating artery and the blood stream in the left anterior cerebral artery was increased. By utilizing this phenomenon, the balloon was guided to the left anterior cerebral artery. After the angiography, the balloon catheter could be withdrawn smoothly without being caught on the intravenous teflon sheathed needle acting as the introducing catheter.

EXAMPLE 8

A polyethylene catheter having an outer diameter of 2.1 mm and an inner diameter of 1.6 mm was inserted from the right femoral artery of a patient suffering from cerebral arteriovenous malformation, and under X-ray fluoroscopy, the polyethylene catheter was guided to the left vertebral artery. Through this catheter, the balloon catheter prepared in Example 3 was inserted into the vertebral artery. Then, the balloon was inflated and the catheter was forwarded to the periphery while the balloon was carried by the blood stream in the floating state. The balloon was passed through the vertebral artery and the basilar artery and then guided to the left posterior cerebral artery. A pinhole had been formed on the balloon in advance. The roentgenography was continuously carried out by injecting 2 cc of a contrast medium through this pinhole. A very good superselective image of the posterior cerebral artery was obtained. No complication was observed.

Obviously, numerous additional modifications and variations of the present invention are possible in light of the above teachings. It is therefore to be understood that within the scope of the appended claims, the invention may be practiced otherwise than as specifically described herein.

What is claimed is:

1. A balloon catheter comprising:
   a tubular catheter having an outer surface and an end portion;
   an inflatable balloon having an outer surface and mounted on said end portion of said catheter so that a fluid is introduced into the balloon from the catheter;
   said catheter further comprising a fine tube having an outer diameter of 100 to 1000$\mu$ and a wall thickness of 10 to 400$\mu$;
   said balloon comprising an elastomer having a wall thickness less than 500$\mu$ in a non-inflated state;
   said balloon being attached to the catheter so as to surround the outer surface of said end portion of the catheter;
   adhesive means for securing said balloon to said outer surface of said end portion of the catheter; and
   a resin layer formed on the outer surface of the catheter adjacent said end portion of the catheter so as to form a smooth surface contiguous to and located between said outer surface of said balloon and the outer surface of the catheter.

2. A balloon catheter as set forth in claim 1, the resin layer comprising an epoxy resin.

3. A balloon catheter as set forth in claim 1, the adhesive means comprising a cyano acrylate type adhesive.

4. A balloon catheter as set forth in claim 1, wherein the fine tube has a Young's modulus of 1 to 100 Kg as measured at 25° C. in the wet state.

5. A balloon catheter as set forth in claim 4, the fine tube comprising acetalized polyvinyl alcohol.

6. A balloon catheter as set forth in claim 5, the acetalized polyvinyl alcohol comprising polyvinyl alcohol in which 20 to 50 mol % hydroxyl groups of polyvinyl alcohol are formalized.

7. A balloon catheter as set forth in claim 1, wherein a small pin hole is positioned on a leading surface of said balloon for injecting a contrast medium into a blood vessel to facilitate an angiograph.

* * * * *

UNITED STATES PATENT AND TRADEMARK OFFICE
CERTIFICATE OF CORRECTION

PATENT NO. : 4,301,803
DATED : NOVEMBER 24, 1981
INVENTOR(S) : HAJIME HANDA ET AL.

It is certified that error appears in the above—identified patent and that said Letters Patent is hereby corrected as shown below:

Column 1, lines 35 and 36, change "roentgengraphy" to --roentgenography--,

Column 3, line 36, insert a comma between synthetic rubbers and silicone rubbers, Column 10, line 52, change "angiograph" to --angiography--.

Column 8, line 16, change "formal" to --femoral--.

Signed and Sealed this

Twenty-eighth Day of December 1982

[SEAL]

Attest:

GERALD J. MOSSINGHOFF

Attesting Officer  Commissioner of Patents and Trademarks